United States Patent [19]

Ikejiri et al.

[11] Patent Number: 5,605,892
[45] Date of Patent: Feb. 25, 1997

[54] COMPOSITIONS OF ARGININE AMIDE WITH CYCLODEXTRIN OF CAFFEINE, AND METHODS OF USE

[75] Inventors: Yoshifumi Ikejiri, Ibaraki; Shirou Sawa, Kobe, both of Japan

[73] Assignees: Senju Pharmaceutical Co., Ltd., Osaka; Mitsubishi Chemical Corporation, Tokyo, both of Japan

[21] Appl. No.: 626,146

[22] Filed: Apr. 5, 1996

Related U.S. Application Data

[63] Continuation of Ser. No. 229,767, Apr. 19, 1994, abandoned.

[30] Foreign Application Priority Data

Apr. 22, 1993 [JP] Japan ..................... 5-096275
Dec. 22, 1993 [JP] Japan ..................... 5-324760

[51] Int. Cl.$^6$ ............... A61K 31/715; A61K 31/555; A61K 31/52
[52] U.S. Cl. ............... 514/58; 514/187; 514/263; 544/274; 536/103; 546/172
[58] Field of Search ............... 514/58, 187, 263; 544/274; 536/103; 546/172

[56] References Cited

U.S. PATENT DOCUMENTS

| | | | |
|---|---|---|---|
| 3,607,287 | 9/1971 | Bohm | 430/164 |
| 4,517,995 | 5/1985 | Lyles | 131/334 |
| 4,728,509 | 3/1988 | Shimizu et al. | 514/291 |
| 5,024,998 | 6/1991 | Bodor | 514/58 |
| 5,180,747 | 1/1993 | Matsuda et al. | 514/681 |
| 5,256,316 | 10/1993 | Suzuki et al. | 252/79.1 |
| 5,324,718 | 6/1994 | Loftsson | 514/58 |
| 5,356,897 | 10/1994 | Oku et al. | 514/258 |

FOREIGN PATENT DOCUMENTS

| | | |
|---|---|---|
| 2091715 | 9/1993 | Canada . |
| 0008746 | 3/1980 | European Pat. Off. . |
| 0301970 | 2/1989 | European Pat. Off. . |
| 0565897 | 10/1993 | European Pat. Off. . |

OTHER PUBLICATIONS

Herrman et al. *Drugs* Jul. 1993, 46(1), 18–52.

*Primary Examiner*—John Kight
*Assistant Examiner*—Kathleen Kahler Fonda
*Attorney, Agent, or Firm*—Wenderoth, Lind & Ponack

[57] ABSTRACT

An aqueous agent comprising at least one arginine amide selected from the group consisting of (2R,4R)-4-methyl-1-[$N^2$-((RS)-3-methyl-1,2,3,4-tetrahydro-8-quinolinesulfonyl)-L-arginyl]-2-piperidinecarboxylic acid, monohydrate thereof and pharmacologically acceptable salts thereof, and at least one compound selected from the group consisting of cyclodextrin and caffeine; a method for improving the solubility of arginine amide in water, comprising adding at least one compound selected from the group consisting of cyclodextrin and caffeine; and a method for stabilizing arginine amide in water, comprising adding caffeine. According to the present invention, the solubility of arginine amide in water can be enhanced to, for example, a concentration permitting inhibition of fibrin formation at the time of entoptic operation. In addition, the stability of arginine amide in water can be enhanced with less irritation of the eye.

7 Claims, No Drawings

COMPOSITIONS OF ARGININE AMIDE WITH CYCLODEXTRIN OF CAFFEINE, AND METHODS OF USE

This application is a continuation of now abandoned application Ser. No. 08/229,767, filed Apr. 19, 1994.

FIELD OF THE INVENTION

The present invention relates to an aqueous agent containing at least one arginine amide selected from (2R,4R)-4-methyl-1-[$N^2$-((RS)-3-methyl-1,2,3,4-tetrahydro-8-quinolinesulfonyl)-L-arginyl]-2-piperidinecarboxylic acid, monohydrate thereof and pharmacologically acceptable salts thereof, which is useful as an active ingredient for inhibiting formation of fibrin in, for example, an entoptic operation, wherein the effective utility of arginine amide as a medicament has been improved. More specifically, the present invention relates to an aqueous composition wherein an arginine amide shows an improved solubility and to an aqueous composition wherein an arginine amide shows an improved stability. Further, the present invention relates to a method for improving the effective utility of arginine amide as a medicament, particularly to a method for improving the solubility of arginine amide and a method for improving the stability thereof.

BACKGROUND OF THE INVENTION

Conventionally, steroid or indomethacin is administered after an entoptic operation of cataract, corpus vitreum, glaucoma or the like, for the reason that fibrin is formed with considerable frequency to cause postoperative complications. However, administration of said compounds for a few weeks after the operation has not shown dependable effects, but causes, though not often, delay in healing of wounds or disorders in cornea.

Fibrin is formed from fibrinogen by the cleavage of arginine-glycoside linkage of fibrinogen by thrombin. Since the aforementioned arginine amide has a potent selective antithrombin action (Japanese Patent Publication No. 48829/1986), the compound is expected to be useful as an eye drop or entoptic perfusate to inhibit formation of fibrin in an entoptic operation.

Taking one of the aforementioned arginine amides, (2R, 4R)4-methyl-1-[$N^2$-((RS)-3-methyl-1,2,3,4-tetrahydro-8-quinolinesulfonyl)-L-arginyl]-2-piperidinecarboxylic acid monohydrate (generally called argatroban) as an example, it is used at a concentration of 1 mg/ml or above as an eye drop or entoptic perfusate for the above-mentioned purpose. Said argatroban has an extremely low solubility in water, showing about 0.9 mg/ml of solubility at 25° C. in the pH range (7.2–7.8) preferable for the administration to local eye sites. Hence, it is necessary to improve the solubility and, as a consequence, the usefulness of argatroban as a medicament. While an aqueous solution of argatroban can be preserved stably in a brown bottle, an improved stability thereof will result in a still greater utility of argatroban as a medicament.

Heretofore, arginine amides are known to be dissolved by a method including addition of sugar and alcohol (U.S. Pat. No. 5,214,052).

In view of the extremely high sensitivity to irritation that the local eye sites such as cornea exhibit, such method of adding sugar and alcohol is not desirable, since sugar and alcohol per se are irritant to the eye and these compounds are added in greater amounts. Consequently, there is practically no aqueous agent satisfactory as an eye drop or an entoptic perfusate containing arginine amide, particularly argatroban.

An object of the present invention is to provide an aqueous agent containing arginine amide improved in the effective utility as a medicament, particularly an aqueous agent of arginine amide having an improved solubility and an aqueous agent of arginine amide showing an improved stability.

Another object of the present invention is to provide a method for improving the effective utility of arginine amide as a medicament in an aqueous agent thereof, specifically a method for improving the solubility of arginine amide and a method for achieving a high stability thereof.

SUMMARY OF THE INVENTION

It has now been found that cyclodextrin or caffeine remarkably improves the solubility of arginine amide, particularly argatroban, in water even with a small amount thereof, that caffeine remarkably improves stability of arginine amide, particularly argatroban, against light in water even with a small amount thereof, and that an aqueous agent containing an arginine amide added with caffeine and/or cyclodextrin causes less eye irritation.

Accordingly, the present invention provides an aqueous agent comprising at least one arginine amide selected from the group consisting of (2R,4R)-4-methyl-1-[$N^2$-((RS)-3-methyl1,2,3,4-tetrahydro-8-quinolinesulfonyl)-L-arginyl]-2-piperidinecarboxylic acid of the formula

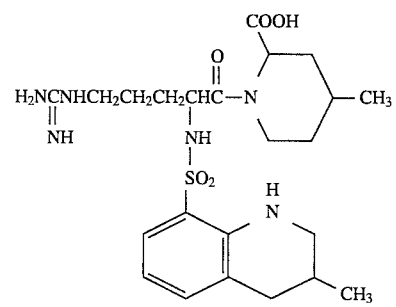

monohydrate thereof and pharmacologically acceptable salts thereof, and at least one compound selected from cyclodextrin and caffeine.

Also, the present invention provides a method for improving the solubility of arginine amide in water, comprising adding at least one compound selected from the group consisting of cyclodextrin and caffeine.

Furthermore, the present invention provides a method for stabilizing arginine amide in water, comprising adding caffeine.

DETAILED DESCRIPTION OF THE INVENTION

The pharmacologically acceptable salts of arginine amide to be used in the present invention are salts with inorganic acid such as hydrochloride, sulfate, hydrobromide and phosphate; salts with organic acid such as fumarate, tartrate, succinate, citrate and methanesulfonate; alkali metal salts such as sodium salt and potassium salt; alkaline earth salts such as calcium salt; and other salts such as ammonium salt. The preferable arginine amide is argatroban.

The aqueous composition of the present invention is preferably used as an eye drop or an entoptic perfusate, In the present invention, improvement in the solubility of arginine amide in water is achieved by adding at least one compound selected from cyclodextrin and caffeine.

So as to improve the stability of arginine amide in water, caffeine is added in the present invention.

The aqueous composition of the present invention can be obtained by dissolving arginine amide and the aforementioned compound(s) in water. When using as an eye drop, the arginine amide is contained in the aqueous composition of the present invention generally at a concentration of about 0.01(W/V) %–1 (W/V) %, preferably about 0.05 (W/V) %–0.5 (W/V) % and when using as an entoptic perfusate, it is contained generally at a concentration of about 0.0001 (W/V) %–1 (W/V) %, preferably about 0.001 (W/V) %–0.5 (W/V) %.

The cyclodextrin to be used in the present invention may be α-compound, β-compound or γ-compound with preference given to β-compound.

The cyclodextrin is generally added at a concentration of 0.01–20 (W/V) %, preferably about 0.05–10 (W/V) %, with variation depending on the kind of cyclodextrin to be used in the present invention. The caffeine is added at a concentration of 0.01–3.0 (W/V) %, preferably about 0.05–2.0 (W/V) %. When added in the specified amounts, the solubility and stability of arginine amide are improved.

The aqueous composition of the present invention may contain the following various additives usable for aqueous agents, particularly for eye drop and entoptic perfusate.

As a buffer, usable are, for example, phosphate buffer, borate buffer, citrate buffer, tartrate buffer, acetate buffer and amino acid.

As an isotonizing agent, usable are, for example, sugars such as sorbitol, glucose and mannitol, polyhydric alcohols such as glycerine and propylene glycol, and salts such as sodium chloride.

As an antiseptic, usable are, for example, quaternary ammonium salts such as benzalkonium chloride and benzethonium chloride, p-oxybenzoic acid esters such as methyl p-oxybenzoate and ethyl p-oxybenzoate, benzyl alcohol, phenethyl alcohol and sorbic acid and salts thereof, thimerosal and chlorobutanol.

As a thickener, usable are, for example, hydroxyethyl cellulose, hydroxypropyl cellulose, methyl cellulose, hydroxypropyl methyl cellulose, carboxymethyl cellulose and salts thereof.

When the aqueous composition of the present invention is used as an eye drop, the pH thereof is generally about 3–9, preferably about 4–8 and when used as an entoptic perfusate, the pH thereof is generally about 6–8.5, preferably about 7–8.

While the method for producing an aqueous agent of the present invention differs depending on the kind of the agent methods known per se can be used for each liquid agent.

The present invention is described in further detail by the illustration of examples and reference example.

EXAMPLE 1

Solubility Test

The solubility of argatroban in water was determined by the use of various compounds.

An excess amount of argatroban was added to a phosphate buffer (pH 7.0) containing a compound at a concentration of 1.0 W/V % and the mixture was shaken at 25° C. for 12 hours. The amount of the argatroban dissolved in this solution was measured by HPLC to determine the solubility. The results are shown in Table 1.

TABLE 1

| Compound | Amount added (W/V %) | Solubility (%) |
| --- | --- | --- |
| Not added | — | 0.0930 |
| α-cyclodextrin | 1.0 | 0.1340 |
| β-cyclodextrin | 1.0 | 0.2590 |
| γ-cyclodextrin | 1.0 | 0.1324 |
| caffeine | 1.0 | 0.2001 |

As is evident from the results in Table 1, α-cyclodextrin, β-cyclodextrin, γ-cyclodextrin and caffeine showed superior improvement in solubility. In particular, β-cyclodextrin afforded about thrice and caffeine afforded about twice the solubility of argatroban obtained when no compound was added.

Reference Example 1 to be mentioned later clearly indicates that fibrin formation was inhibited by about 50% by the argatroban concentration of 0.1 W/V % and fibrin formation was completely inhibited by the argatroban concentration of 0.2 W/V %.

It should be understood that the addition of cyclodextrin and/or caffeine, particularly caffeine and β-cyclodextrin, contributes to the clinically effective concentration of argatroban.

Eye irritation caused by the respective, aforementioned solutions of α-cyclodextrin, β-cyclodextrin, γ-cyclodextrin and caffeine was examined using house rabbits. As a result, there was found no specific problems, thus showing no harmful effect on the eye tissue.

Based on the test results given above, it was found that the use of cyclodextrin and/or caffeine was conducive to the remarkably notable improvement in solubility.

EXAMPLE 2

Stability Test

Aqueous solutions (pH 7) containing 0.05 W/V % or 0.1 W/V % argatroban and having the formulations 1–6 shown in Table 2 below were filled in glass ampoules and preserved in shade or under light exposure of 600,000 lux per hour. Each solution was examined for pH, appearance, insoluble matter and residual content of argatroban. The results are shown in Table 3.

TABLE 2

| 0.05 W/V % argatroban aqueous solution | Formulation 1 | Formulation 2 | Formulation 3 |
| --- | --- | --- | --- |
| Argatroban | 0.05% | 0.05% | 0.05% |
| Caffeine | — | 0.25% | 0.5% |
| Sodium dihydrogenphosphate | 0.1% | 0.1% | 0.1% |
| 0.1% argatroban aqueous solution | Formulation 4 | Formulation 5 | Formulation 6 |
| Argatroban | 0.1% | 0.1% | 0.1% |
| Caffeine | — | 0.5% | 1.0% |
| Sodium dihydrogenphosphate | 0.1% | 0.1% | 0.1% |

Note: % = W/V %

TABLE 3

Stability of aqueous solution of argatroban (pH 7) against light

| | Appearance | pH | Residual content (%) |
|---|---|---|---|
| Formulation 1 | | | |
| (shading) | colorless and clear | 7.05 | 100 |
| (exposed to light) | light brown and slightly turbid | 6.83 | 32.1 |
| Formulation 2 | | | |
| (shading) | colorless and clear | 7.04 | 100 |
| (exposed to light) | light brown and slightly turbid | 6.93 | 73.6 |
| Formulation 3 | | | |
| (shading) | colorless and clear | 7.08 | 100 |
| (exposed to light) | light brown and slightly turbid | 7.01 | 78.7 |
| Formulation 4 | | | |
| (shading) | colorless and clear | 7.00 | 100 |
| (exposed to light) | light brown and slightly turbid | 6.88 | 66.3 |
| Formulation 5 | | | |
| (shading) | colorless and clear | 7.00 | 100 |
| (exposed to light) | light brown and slightly turbid | 6.97 | 82.1 |
| Formulation 6 | | | |
| (shading) | colorless and clear | 7.00 | 100 |
| (exposed to light) | light brown and slightly turbid | 6.99 | 87.6 |

As is evident from the results in Table 3, the stability of argatroban against light was improved by caffeine.

Reference Example—Argatroban concentration and inhibition of fibrin formation in anterior sac Animal used: 18 colored house rabbits weighing 2 kg and showing no abnormality in the eyes by visual observation
Drug used: test drug (a solution of argatroban at a concentration of 0.1 W/V % or 0.2 W/V % prepared according to the eye drop of Example 1)
: control (physiological saline)
Test: Fibrin was formed in anterior sac by irradiation at four sites in iris with argon laser (AC-3500, Nidek). The irradiation was conducted at a spot size of 100 μm, time 0.2 sec and output 1 watt. The fibrin in anterior sac was evaluated according to the evaluation criteria given below for the visual observation with time with a slit lamp after the irradiation up to 3 hours thereafter.

The test drug argatroban was administered 7 times by installation of 50 μl of the drug to one of the eyes every 10 minutes beginning from 30 minutes before the laser irradiation to 30 minutes after the irradiation, and physiological saline was administered to the other eye.

Slit lamp observation: The presence of fibrin at the 4 sites irradiated with laser was graded (0 or 1). When the fibrin amount was great, the grade was doubled. The fibrin in pupil region was graded in five stages of from 0 to 4 points. The full mark was; irradiation site: 4 points×2+pupil region: 4 points=12 points.

Test Results

The fibrin amount in anterior sac in the control group reached maximum at 0.5 hour after the laser irradiation and fibrin disappeared with time in 1 hour. The test drug at a concentration of 0.1 W/V % significantly inhibited the fibrin formation at every measurement point. The percent inhibition was about 50%. The test drug completely inhibited the fibrin formation at a concentration of 0.2 W/V %.

Formulation Example 1—eye drop

An eye drop was prepared according to the following formulation.

| Argatroban | 0.2 g |
|---|---|
| Caffeine | 0.5 g |
| Polysorbate 80 | 0.1 g |
| Benzalconium chloride | 0.01 g |
| Sodium dihydrogenphosphate | 0.1 g |
| Sodium chloride | 0.8 g |
| 1 N Hydrochloric acid | 1 ml |
| Sodium hydroxide | appropriate amount |
| Sterile purified water | appropriate amount |
| Total | 100 ml (pH 7) |

Formlation Example 2—eye drop

An eye drop was prepared according to the following formulation.

| Argatroban | 0.2 g |
|---|---|
| β-cyclodextrin | 1.0 g |
| Boric acid | 1.8 g |
| Sodium tetraborate | 0.5 g |
| Sodium hydroxide | appropriate amount |
| Sterile purified water | appropriate amount |
| Total | 100 ml (pH 7) |

Formulation Example 3—entoptic perfusate

An entoptic perfusate was prepared according to the following formulation.

| Argatroban | 0.15 g |
|---|---|
| Glucose | 0.15 g |
| Caffeine | 0.5 g |
| Sodium chloride | 0.6 g |
| Potassium chloride | 0.05 g |
| Calcium chloride | 0.02 g |
| Magnesium sulfate | 0.03 g |
| Sodium hydrogencarbonate | 0.2 g |
| Hydrochloric acid | appropriate amount |
| Sterile purified water | appropriate amount |
| Total | 100 ml (pH 7.5) |

According to the aqueous agent of the present invention, the solubility of arginine amide in water can be enhanced by the use of at least one compound selected from cyclodextrin and caffeine. Accordingly, the concentration thereof can be increased to, for example, a concentration permitting inhibition of fibrin formation at the time of entoptic operation. In addition, the use of caffeine with arginine amide results in enhanced stability of arginine amide against light.

Consequently, the effective utility of arginine amide as a medicament can be enhanced by the present invention.

What is claimed is:

1. An aqueous agent consisting essentially of at least one arginine amide selected from the group consisting of (2R, 4R)-4-methyl-1-{$N^2$-((RS)-3-methyl-1,2,3,4-tetrahydro-8-quinolinesulfonyl)-L-arginyl]-2-piperidinecarboxylic acid, the monohydrate thereof or a pharmacologically acceptable salt thereof at a concentration of 0.1–1 (W/V) %, at least one compound selected from the group consisting of cyclodextrin and caffeine, and at least one pharmaceutically acceptable additive selected from the group consisting of a buffer, an isotonizing agent, an antiseptic and a thickener, the concentration of said cyclodextrin, when present, being from 0.05–10 (W/v) % and the concentration of said caffeine, when present, being from 0.05–2.0 (W/V) %.

2. The aqueous agent of claim 1, wherein the cyclodextrin is a β-compound.

3. The aqueous agent of claim 1, having a pH of 3–9.

4. The aqueous agent of claim 1, having a pH of 6–8.5.

5. A method for improving the aqueous solubility of an arginine amide, comprising adding at least one compound selected from the group consisting of cyclodextrin and caffeine to an aqueous solution comprising at least one arginine amide selected from the group consisting of (2R,4R)-4-methyl-1-[$N^2$-((RS)-3-methyl-1,2,3,4-tetrahydro-8-quinolinesulfonyl)-L-arginyl]-2-piperidinecarboxylic acid, the monohydrate thereof or a pharmacologically acceptable salt thereof at a concentration of 0.1–1(W/V) %, and at least one pharmaceutically acceptable additive selected from the group consisting of a buffer, an isotonizing agent, an antiseptic and a thickener, the concentration of said cyclodextrin, when present, being from 0.05–10 (W/V) % and the concentration of said caffeine, when present, being from 0.05–2.0 (W/V) %.

6. A method for stabilizing an arginine amide to light comprising adding caffeine to an aqueous solution comprising at least one arginine amide selected from the group consisting of (2R,4R)-4-methyl-1-[$N^2$-((RS)-3-methyl-1,2,3,4-tetrahydro-8-quinolinesulfonyl)-L-arginyl]-2-piperidinecarboxylic acid, the monohydrate thereof or a pharmacologically acceptable salt thereof at a concentration of 0.05–1(W/V) %, and at least one pharmaceutically acceptable additive selected from the group consisting of a buffer, an isotonizing agent, an antiseptic and a thickener, the concentration of said caffeine being from 0.05–2.0(W/V) %.

7. A method for inhibiting fibrin formation in the eye of a patient following eye surgery which comprises topically administering to the eye of said patient following said surgery an effective amount of an aqueous agent as defined in claim 1.

* * * * *